(12) United States Patent
Cho et al.

(10) Patent No.: US 10,918,725 B2
(45) Date of Patent: Feb. 16, 2021

(54) OPHTHALMIC COMPOSITION COMPRISING REBAMIPIDE AND METHOD FOR PREPARING THE SAME

(71) Applicant: SAMJIN PHARMACEUTICAL CO., LTD., Seoul (KR)

(72) Inventors: Eui-Hwan Cho, Seoul (KR); Sung-Ju Choi, Seoul (KR); Sung-Woo Lee, Seoul (KR); Hee-Jong Shin, Gyeonggi-do (KR); Min-Hyo Ki, Chungcheong-nam-do (KR); Mee-Hwa Choi, Gyeonggi-do (KR); Dong-Ha Lee, Gyeonggi-do (KR)

(73) Assignee: SAMJIN PHARMACEUTICAL CO., LTD., Seoul (KR)

( * ) Notice: Subject to any disclaimer, the term of this patent is extended or adjusted under 35 U.S.C. 154(b) by 0 days.

(21) Appl. No.: 15/762,165

(22) PCT Filed: Sep. 30, 2016

(86) PCT No.: PCT/KR2016/011015
§ 371 (c)(1),
(2) Date: Mar. 22, 2018

(87) PCT Pub. No.: WO2017/057973
PCT Pub. Date: Apr. 6, 2017

(65) Prior Publication Data
US 2018/0264120 A1 Sep. 20, 2018

(30) Foreign Application Priority Data

Oct. 1, 2015 (KR) .................. 10-2015-0138349

(51) Int. Cl.
*A61K 47/40* (2006.01)
*A61K 9/48* (2006.01)
*A61K 9/08* (2006.01)
*A61K 31/4704* (2006.01)
*A61K 47/02* (2006.01)
*A61K 47/10* (2017.01)
*A61K 47/18* (2017.01)
*A61K 47/22* (2006.01)
*A61K 47/32* (2006.01)
*A61K 47/34* (2017.01)
*A61K 47/38* (2006.01)
*A61K 9/00* (2006.01)
*A61K 47/44* (2017.01)

(52) U.S. Cl.
CPC ............ *A61K 47/40* (2013.01); *A61K 9/0048* (2013.01); *A61K 9/08* (2013.01); *A61K 31/4704* (2013.01); *A61K 47/02* (2013.01); *A61K 47/10* (2013.01); *A61K 47/18* (2013.01); *A61K 47/183* (2013.01); *A61K 47/22* (2013.01); *A61K 47/32* (2013.01); *A61K 47/34* (2013.01); *A61K 47/38* (2013.01); *A61K 47/44* (2013.01)

(58) Field of Classification Search
CPC combination set(s) only.
See application file for complete search history.

(56) References Cited

U.S. PATENT DOCUMENTS

| 5,576,311 A | 11/1996 | Guy |
| 2007/0287729 A1 | 12/2007 | Matsuda et al. |
| 2010/0029714 A1 | 2/2010 | Masuda |
| 2011/0021974 A1* | 1/2011 | Shantha .............. A61K 9/0048 604/20 |
| 2011/0124682 A1* | 5/2011 | Sumida ............... A61K 9/0048 514/312 |
| 2014/0294991 A1* | 10/2014 | Takeji ................ A61K 31/4704 424/641 |

FOREIGN PATENT DOCUMENTS

| CA | 2851095 A1 | 5/2013 |
| CN | 101081211 A | 12/2007 |
| CN | 101757621 A | 6/2010 |
| CN | 102512420 A | 6/2012 |
| CN | 103945846 A | 7/2014 |
| CN | 104586762 A | 5/2015 |
| CN | 105147606 A | 12/2015 |
| JP | 1994016547 A | 1/1994 |
| JP | 2007532648A A1 | 6/2008 |
| JP | WO2011016562 A1 | 7/2009 |
| JP | 2011524854 A | 9/2011 |
| KR | 20040104020 A | 12/2004 |
| KR | 20150063084 A | 6/2015 |
| KR | 1718733B B1 | 3/2017 |
| RU | 2398585 C2 | 9/2010 |
| RU | 2467751 C2 | 11/2012 |
| WO | 9713515 A1 | 4/1997 |
| WO | WO2005105067 A1 | 11/2005 |
| WO | 2006052018 A1 | 5/2006 |
| WO | 2008050896 A1 | 5/2008 |
| WO | 2008074853 A1 | 6/2008 |
| WO | 2009022674 A1 | 2/2009 |
| WO | WO-2009022674 A1 * | 2/2009 ........... A61K 47/183 |
| WO | 2009108077 A2 | 9/2009 |
| WO | 2009154304 A2 | 12/2009 |
| WO | 2013065866 A1 | 5/2013 |
| WO | 2014051163 A1 | 4/2014 |

OTHER PUBLICATIONS

International Search Report dated Dec. 8, 2016 for International Application No. PCT/KR2016/011015 filed Sep. 30, 2016.

(Continued)

*Primary Examiner* — Jared Barsky
(74) *Attorney, Agent, or Firm* — Blue Filament Law PLLC

(57) ABSTRACT

An ophthalmic composition is provided that includes rebamipide and a method for preparing the same. The ophthalmic composition of maintains its transparency for a long time even in a physiologically neutral to weakly basic pH range that does not injure the cornea and conjunctiva of a patient suffering from dry eye and has improved stability so as not to be re-dispersed.

7 Claims, No Drawings

(56) References Cited

OTHER PUBLICATIONS

Uekama, K., "Control of Drug Release by Cyclodextrins", Fragrance Journal, 1991, pp. 22-27, vol. 19, No. 3.
English translation of Japanese Notice of Reasons for Rejection dated Dec. 25, 2018 for Japanese Application No. 2018-516690 filed Sep. 30, 2016.
English translation of Russian Search Report dated Feb. 6, 2019 for Russian Application No. 2018115669/04 (024441) filed Sep. 30, 2016.
Requisition by the Examiner dated Mar. 26, 2019 for Canadian Application No. 3,000,634 filed Sep. 30, 2016.
Supplementary European Search Report dated May 6, 2019 for European Application No. 16852119 filed Sep. 30, 2016.
First Office Action issued in corresponding Chinese Patent Appln. No. 2016800562059, dated Apr. 30, 2020.
Luo, Mingsheng et.al., "A Complete Works of Pharmacy Excipients", SiChuan Science and Technology Press, 2006, pp. 1237-1238 (with English translation).

\* cited by examiner

OPHTHALMIC COMPOSITION COMPRISING REBAMIPIDE AND METHOD FOR PREPARING THE SAME

TECHNICAL FIELD

The present disclosure relates to an ophthalmic composition comprising rebamipide, which maintains its transparency, has excellent stability, and is easy to prepare, and a method for preparing the same.

BACKGROUND ART

Rebamipide [2-(4-chlorobenzoylamino)-3-(2-quinolon-4-yl)propionic acid] is a quinolone derivative represented by the following formula I.

[Formula 1]

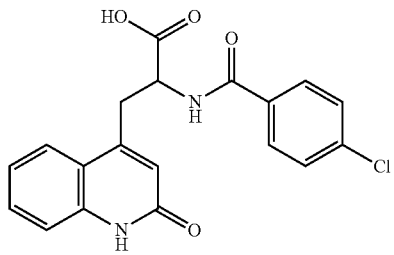

Rebamipide is known to increase gastric mucin to have anti-inflammatory and antiulcer actions on the digestive tract and thus has been used as an oral therapeutic agent for gastric ulcer since 1990. Moreover, the effects of rebamipide on an increase of goblet cell density in eyes, an increase of mucin in eyes, and an increase of lacrimal fluid have been proven, and thus rebamipide has been developed and sold as a therapeutic agent for dry eye syndrome in the form of an ophthalmic solution in Japan.

However, rebamipide has low solubility in a pH range where it is applicable to the eye, which makes it difficult to maintain a stable and transparent aqueous solution during long-term storage and to manufacture in the form of a transparent ophthalmic solution, and thus is available in the form of an ophthalmic suspension. Moreover, in the commercially available ophthalmic suspensions, the drug is dispersed as particles, which causes a feeling of irritation in the eye as well as local pain. Research aimed at developing a transparent ophthalmic solution comprising rebamipide has continued to progress; however, it is believed that it is difficult to develop an aqueous preparation comprising rebamipide so far, and the products developed so far are in the form of an ophthalmic suspension.

International Patent Publication No. WO 97/013515 discloses an aqueous suspension containing rebamipide. However, this suspension may form a flocculated suspension when standing for a long time. Therefore, the suspension needs to be shaken well to disperse the flocculated suspension. Moreover, the above suspension is a white suspension and thus may obscure the view.

International Patent Publication No. WO 2008/050896 discloses a rebamipide-containing aqueous suspension with improved suspensibility which can keep the dispersed fine-particle state of rebamipide stable without having the fine particle agglutinated, compared to the aqueous suspension of the above-mentioned International Patent Publication No. WO 97/013515. However, this suspension may also form a precipitate when standing for a long time and is a white suspension that obscures the view.

International Patent Publication No. WO 2006/052018 discloses an aqueous suspension containing crystalline rebamipide which has improved transparency, compared to the above-mentioned two aqueous suspensions. However, this invention requires expensive equipment such as a high-pressure homogenizer, a colloid mill, an ultrasonic device, etc. during manufacturing, the manufacturing process is very difficult and complicated, and the manufacturing time is long, resulting in high manufacturing costs. Moreover, it also has the problem that it forms a precipitate when standing for a long time.

International Patent Publication No. WO 2009/154304 and International Patent Publication No. WO 2014/051163 disclose transparent rebamipide ophthalmic compositions. However, these ophthalmic solutions have a high pH of 8 or higher and are not suitable for a patient suffering from an injury in cornea and conjunctiva such as dry eye.

Moreover, International Patent Publication No. WO 2008/074853 discloses a composition which uses a viscosity enhancer and a buffer to maintain the stability of an aqueous solution comprising rebamipide. However, this composition also has the problem that it forms a precipitate when standing for a long time.

Therefore, it is necessary to develop a pharmaceutical composition comprising rebamipide, which maintains its transparency for a long time even in a physiologically neutral to weakly basic pH range (below 8) that does not injure the cornea and conjunctiva of a patient suffering from dry eye, and which has improved stability so as not to be re-dispersed.

DISCLOSURE OF INVENTION

Technical Problem

An object of the present disclosure is to provide an ophthalmic composition comprising rebamipide, which is transparent in a pH range of 7 to 8. More specifically, an object of the present disclosure is to provide an ophthalmic composition comprising rebamipide, which maintains its transparency for a long time even in a physiologically neutral to weakly basic pH range that does not injure the cornea and conjunctiva of a patient suffering from dry eye, and which has improved stability so as not to be re-dispersed.

Moreover, another object of the present disclosure is to provide a method for preparing an ophthalmic composition of the present disclosure in a simple manner without any complicated process.

Solution to Problem

In order to accomplish the objects of the present disclosure, the present disclosure provides a novel ophthalmic composition comprising rebamipide and a method for preparing the same, which will be described in detail below.

Ophthalmic Composition Comprising Rebamipide

The ophthalmic composition of the present disclosure comprises (1) rebamipide, (2) an anti-recrystallizing agent selected from the group consisting of a cyclodextrin derivative, an amino acid, and mixtures thereof, and (3) a buffering agent.

Rebamipide may be prepared directly by a conventionally known method or commercially available.

In the present disclosure, the concentration of rebamipide may be 0.1 to 1.5 w/v %, preferably 0.2 to 1.0 w/v %.

The anti-recrystallizing agent used in the present disclosure is an additive to prevent a solution, which is sufficiently transparent but is present in a supersaturated state, from failing to maintain a transparent appearance without any precipitate being formed during long-term storage. The anti-recrystallizing agent that can be used in the present disclosure includes a cyclodextrin derivative and/or an amino acid.

Examples of the cyclodextrin derivative used as the anti-recrystallizing agent in the present disclosure include alpha-, beta-, and gamma-cyclodextrin, and substituted derivatives thereof such as dimethyl-, hydroxyethyl-, hydroxypropyl-, or sulfobutylether-beta-cyclodextrin. Hydroxypropylbetadex may preferably be used. Moreover, the concentration of the cyclodextrin derivative may preferably be 1.0 to 10.0 w/v %.

The amino acid that is another anti-recrystallizing agent of the present disclosure may comprise at least one selected from the group consisting of basic amino acids such as arginine, lysine, histidine, etc. and neutral amino acids such as glycine, alanine, valine, etc. Moreover, the concentration of the amino acid may preferably be 0.1 to 5.0 w/v %.

In the present disclosure, the buffering agent may comprise at least one selected from the group consisting of borate, phosphate, tromethamine, and mixtures thereof. Borate may preferably be used as the buffering agent. Moreover, the concentration of the buffering agent may preferably be 0.05 to 2.0 w/v %.

Moreover, the ophthalmic composition of the present disclosure may further comprise at least one additive selected from the group consisting of a thickener, a solubilizing agent, an isotonic agent, and a pH adjusting agent.

The thickener is an additive that extends the amount of time a drug stays in the body during clinical application and may comprise at least one selected from the group consisting of polyvinylpyrrolidone, hydroxypropylmethylcellulose, and polyvinyl alcohol, but not limited thereto. Polyvinylpyrrolidone may preferably be used.

The solubilizing agent is an additive to increase the solubility of a drug and may comprise at least one selected from the group consisting of polyoxyl 35 hydrogenated castor oil, poloxamer, and polysorbate.

The isotonic agent may be added in an amount that makes the osmotic pressure of the ophthalmic solution similar to that of tears and may comprise chlorides, saccharides, propylene glycol, and glycerin.

The pH adjusting agent is an additive to adjust the pH in a range that is applicable to the body (eye) and does not injure the cornea and conjunctiva and may comprise inorganic acids or organic acids. An inorganic acid such as phosphoric acid or phosphate may preferably be used.

The ophthalmic composition of the present disclosure may preferably have a pH of 7 to 8, which is in a physiologically neutral to weakly basic range that does not injure the cornea and conjunctiva of a patient suffering from dry eye.

Moreover, the ophthalmic composition of the present disclosure has excellent transparency in the above pH range (pH 7 to 8), maintains its transparency even after standing for a long time, and has improved stability so as not to be re-dispersed.

According to a preferred embodiment of the present disclosure, the ophthalmic composition of the present disclosure is a solution formulation, rather than the existing aqueous suspension. The ophthalmic composition of the present disclosure has solved the problem that it is difficult to manufacture in the form of a solution due to low solubility and, at the same time, has ensured the excellent transparency and stability. Therefore, the ophthalmic composition of the present disclosure may be very useful as an ophthalmic solution to patients suffering from dry eye.

Method for Preparing Ophthalmic Composition Comprising Rebamipide

The method for preparing an ophthalmic composition of the present disclosure comprises: a first step (S-1) of obtaining a solution by dissolving rebamipide in a buffer solution; a second step (S-2) of adding and dissolving an anti-recrystallizing agent selected from the group consisting of a cyclodextrin derivative, an amino acid, and mixtures thereof in the solution obtained in the first step; and a third step (S-3) of filtering the solution obtained in the second step through a sterile filter.

Moreover, the second step may further comprise, after dissolving the anti-recrystallizing agent, the step of adding and dissolving at least one additive selected from the group consisting of a thickener, a solubilizing agent, an isotonic agent, and a pH adjusting agent.

Specifically, a buffer solution of a suitable concentration is prepared by adding a buffering agent, and then rebamipide is added and dissolved in the buffer solution while stirring. The pH adjusting agent may be added as necessary, and the anti-recrystallizing agent is added and dissolved in the transparent rebamipide solution while stirring. The thickener, the solubilizing agent, the pH adjusting agent, and the isotonic agent may be added in appropriate concentrations according to circumstances. Moreover, all of these processes are achieved by simple stirring, and filtration is performed using a 0.22 μm sterile filter to achieve sterilization.

The manufacturing method of the present disclosure uses the anti-recrystallizing agent of rebamipide, such as the cyclodextrin derivative and/or amino acid, and the buffering agent to sufficiently maintain the transparency and prevent the formation of a precipitate layer even during long-term storage and can manufacture the ophthalmic composition comprising rebamipide by simple stirring without the use of expensive equipment.

Pharmaceutical Composition, and Method of Preventing or Treating Dry Eye Syndrome The present disclosure provides a pharmaceutical composition comprising the ophthalmic composition of the present disclosure.

The present disclosure also provides a pharmaceutical composition for treating dry eye syndrome comprising the ophthalmic composition of the present disclosure.

The present disclosure also provides a method of treating dry eye syndrome comprising an administration of the ophthalmic composition of the present disclosure to patients.

Advantageous Effects of Invention

The ophthalmic composition of the present disclosure is prepared by mixing an anti-recrystallizing agent with a composition comprising rebamipide and a buffer solution, and thus it is possible to improve the transparency of the ophthalmic composition and maintain its transparency without aggregation or precipitation of dissolved particles even during long-term storage.

Moreover, according to the present disclosure, it is possible to manufacture a transparent rebamipide ophthalmic solution by simple stirring without requiring complicated manufacturing processes such as high-pressure homogenization, ultrasonic dispersion, etc. by selecting a buffering agent suitable for the composition and adjusting the concentration of the buffer solution. Furthermore, it is possible to remove bacteria only by filtration using a 0.22 μm sterile filter, resulting in reduced manufacturing costs.

MODE FOR THE INVENTION

Hereinafter, Examples and Experimental Examples of the present disclosure will be described below for better understanding of the present disclosure, but the scope of the present disclosure is not limited by the Examples and Experimental Examples.

Examples 1 to 13 and Comparative Examples 1 to 5

According to the composition and ratio of components shown in the following tables 1 and 2, to purified water of appropriate volume, a buffering agent was added while stirring. To the buffer solution while stirring, rebamipide was added and dissolved, and then hydroxypropylbetadex was added thereto. After the rebamipide and hydroxypropylbetadex were completely dissolved, a pH adjusting agent and an isotonic agent were added to adjust the pH level and the osmotic pressure. The resulting rebamipide solution was filtered using a 0.22 μm sterile filter to prepare colorless transparent ophthalmic compositions of Examples 1 to 13.

According to the composition and ratio of components shown in the following tables 1 and 2, compositions of Comparative Examples 1 to 5 were prepared by the same preparation method described in Examples 1 to 13, except for the process of adding hydroxypropylbetadex.

TABLE 1

Compositions I according to the composition of the buffering agent and hydroxypropylbetadex

| Components | Examples | | | | | | Comparative Examples | | |
|---|---|---|---|---|---|---|---|---|---|
| | 1 | 2 | 3 | 4 | 5 | 6 | 1 | 2 | 3 |
| Rebamipide (mg) | 500 | 500 | 500 | 500 | 500 | 500 | 500 | 500 | 500 |
| Hydroxypropyl-betadex (g) | 10 | 10 | 10 | 5 | 5 | 5 | — | — | — |
| Sodium borate (g) | 0.95 | — | — | 0.95 | — | — | 0.95 | — | — |
| Sodium phosphate (g) | — | 0.75 | — | — | 0.75 | — | — | 0.75 | — |
| Tromethamine (g) | — | — | 0.75 | — | — | 0.75 | — | — | 0.75 |
| Sodium chloride or glycerin | q.s | q.s | q.s | q.s | q.s | q.s | q.s | q.s | q.s |
| Phosphoric acid | q.s | q.s | q.s | q.s | q.s | q.s | q.s | q.s | q.s |
| Purified water | q.s | q.s | q.s | q.s | q.s | q.s | q.s | q.s | q.s |
| Total Volume (mL) | | | | | 100 | | | | |
| pH | | | | | about 7.8 | | | | |

TABLE 2

Compositions II according to the composition of the buffering agent and hydroxypropylbetadex

| Components | Examples | | | | | | | Comparative Examples | |
|---|---|---|---|---|---|---|---|---|---|
| | 7 | 8 | 9 | 10 | 11 | 12 | 13 | 4 | 5 |
| Rebamipide (mg) | 500 | 500 | 500 | 500 | 500 | 500 | 500 | 500 | 500 |
| hydroxypropyl-betadex (g) | 2 | 2 | 2 | 5 | 5 | 10 | 10 | — | — |
| Sodium borate (g) | 0.95 | 0.50 | 0.10 | 0.50 | 0.10 | 0.50 | 0.10 | 0.50 | 0.10 |
| Sodium chloride or glycerin | q.s | q.s | q.s | q.s | q.s | q.s | q.s | q.s | q.s |
| Phosphoric acid | q.s | q.s | q.s | q.s | q.s | q.s | q.s | q.s | q.s |
| Purified water | q.s | q.s | q.s | q.s | q.s | q.s | q.s | q.s | q.s |
| Total Volume (mL) | | | | | 100 | | | | |
| pH | | | | | about 7.8 | | | | |

Examples 14 to 21

Compositions of Examples 14 to 21 were prepared by the same preparation method described in Examples 1 to 13, except for varying the composition and ratio of amino acids as shown in the following table 3.

TABLE 3

Composition according to the composition and ratio of amino acids

| Components | Examples | | | | | | | |
|---|---|---|---|---|---|---|---|---|
| | 14 | 15 | 16 | 17 | 18 | 19 | 20 | 21 |
| Rebamipide (mg) | 500 | 500 | 500 | 500 | 500 | 500 | 500 | 500 |
| Arginine (g) | 2.0 | — | 1.0 | — | — | 0.2 | — | — |
| Lysine (g) | — | 2.0 | — | 1.0 | — | — | 0.2 | — |
| Glycine (g) | — | — | — | — | 0.5 | — | — | 0.2 |
| Sodium borate (g) | 0.50 | 0.5 | 0.50 | 0.50 | 0.50 | 0.75 | 0.75 | 0.75 |
| Sodium chloride or glycerin | q.s | q.s | q.s | q.s | q.s | q.s | q.s | q.s |
| Phosphate | q.s | q.s | q.s | q.s | — | — | — | — |
| Phosphoric acid | — | — | — | — | q.s | q.s | q.s | q.s |
| Purified water | q.s | q.s | q.s | q.s | q.s | q.s | q.s | q.s |
| Total volume (mL) | 100 | | | | | | | |
| pH | about 7.8 | | | | | | | |

Examples 22 to 29

Compositions of Examples 22 to 29 were prepared by the same preparation method described in Examples 1 to 13, except for varying the ratio of the thickener that can be further added to the ophthalmic composition comprising the anti-recrystallizing agent and the buffering agent as shown in the following table 4.

TABLE 4

Composition according to the ratio of thickeners

| Components | Examples | | | | | | | |
|---|---|---|---|---|---|---|---|---|
| | 22 | 23 | 24 | 25 | 26 | 27 | 28 | 29 |
| Rebamipide (mg) | 500 | 500 | 500 | 500 | 500 | 500 | 500 | 500 |
| Hydroxypropyl-betadex (g) | 5 | — | 5 | 5 | 5 | 5 | — | — |
| Arginine (g) | — | 1 | 1 | — | 0.2 | — | 1 | — |
| Lysine (g) | — | — | — | 1 | — | 0.2 | — | 1 |
| Sodium borate (g) | 0.50 | 0.50 | 0.50 | 0.50 | 0.75 | 0.75 | 0.50 | 0.50 |
| Polyvinyl-pyrrolidone (g) | 5 | 5 | 5 | 5 | 5 | 5 | — | — |
| Hydroxypropyl-methyl cellulose | — | — | — | — | — | — | 0.5 | 0.5 |
| Sodium chloride or glycerin | q.s | q.s | q.s | q.s | q.s | q.s | q.s | q.s |
| Phosphoric acid | q.s | q.s | q.s | q.s | q.s | q.s | q.s | q.s |
| Purified water | q.s | q.s | q.s | q.s | q.s | q.s | q.s | q.s |
| Total volume (mL) | 100 | | | | | | | |
| pH | about 7.8 | | | | | | | |

Examples 30 to 34

Compositions of Examples 30 to 34 were prepared by the same preparation method described in Examples 1 to 13, except for varying the ratio of the solubilizing agent that can be further added to the composition comprising the anti-recrystallizing agent and the buffering agent as shown in the following table 5.

TABLE 5

Compositions according to the ratio of solubilizing agents

| Components | Examples | | | | |
|---|---|---|---|---|---|
| | 30 | 31 | 32 | 33 | 34 |
| Rebamipide (mg) | 500 | 500 | 500 | 500 | 500 |
| Hydroxypropylbetadex (g) | 2 | 2 | 2 | 2 | 2 |
| Arginine (g) | — | 0.2 | — | 0.2 | — |
| Lysine (g) | — | — | 0.2 | — | 0.2 |
| Polyvinylpyrrolidone (g) | 2 | 2 | 2 | 2 | 2 |
| Sodium borate (g) | 0.95 | 0.95 | 0.95 | 0.95 | 0.95 |
| Polyoxyl 35 hydrogenated castor oil (g) | 0.5 | 0.5 | 0.5 | — | — |
| Poloxamer (g) | — | — | — | 0.1 | 0.1 |
| Sodium chloride | q.s | q.s | q.s | q.s | q.s |
| Phosphoric acid | q.s | q.s | q.s | q.s | q.s |
| Purified water | q.s | q.s | q.s | q.s | q.s |
| Total volume (mL) | 100 | | | | |
| pH | about 7.8 | | | | |

Experimental Example 1

In order to evaluate the transparency and stability depending on the presence or absence of the anti-recrystallizing agent, the compositions prepared in Examples 1 to 13 and Comparative Examples 1 to 5 were stored at room temperature and under refrigeration, and then the presence or absence of crystal precipitation over time was determined and shown in the following tables 6 to 9.

The transparency of the compositions was observed with the naked eye using a tester for the Insoluble Particulate Matter Test for Ophthalmic Solutions of the Korean Pharmacopoeia.

TABLE 6

Evaluation of Stability at Room Temperature of Examples 1 to 13

| | | During Preparation | 1 Week | 2 Weeks |
|---|---|---|---|---|
| Examples | 1 | Transparent liquid | Transparent liquid | Transparent liquid |

TABLE 6-continued

Evaluation of Stability at Room Temperature of Examples 1 to 13

|  | During Preparation | 1 Week | 2 Weeks |
|---|---|---|---|
| 2 | Transparent liquid | Transparent liquid | Transparent liquid |
| 3 | Transparent liquid | Transparent liquid | Transparent liquid |
| 4 | Transparent liquid | Transparent liquid | Transparent liquid |
| 5 | Transparent liquid | Transparent liquid | Transparent liquid |
| 6 | Transparent liquid | Transparent liquid | Transparent liquid |
| 7 | Transparent liquid | Transparent liquid | Transparent liquid |
| 8 | Transparent liquid | Transparent liquid | Transparent liquid |
| 9 | Transparent liquid | Transparent liquid | Transparent liquid |
| 10 | Transparent liquid | Transparent liquid | Transparent liquid |
| 11 | Transparent liquid | Transparent liquid | Transparent liquid |
| 12 | Transparent liquid | Transparent liquid | Transparent liquid |
| 13 | Transparent liquid | Transparent liquid | Transparent liquid |

TABLE 7

Evaluation of Stability at Room Temperature of Comparative Examples 1 to 5

|  |  | During preparation | 1 Week | 2 Weeks |
|---|---|---|---|---|
| Comparative Examples | 1 | Transparent liquid | Transparent liquid | Precipitate formed |
|  | 2 | Transparent liquid | Transparent liquid | Precipitate formed |
|  | 3 | Transparent liquid | Transparent liquid | Precipitate formed |
|  | 4 | Transparent liquid | Transparent liquid | Precipitate formed |
|  | 5 | Transparent liquid | Transparent liquid | Precipitate formed |

TABLE 8

Evaluation of Stability under Refrigeration of Examples 1 to 13

|  |  | During preparation | 1 Week | 2 Weeks |
|---|---|---|---|---|
| Examples | 1 | Transparent liquid | Transparent liquid | Transparent liquid |
|  | 2 | Transparent liquid | Transparent liquid | Transparent liquid |
|  | 3 | Transparent liquid | Transparent liquid | Transparent liquid |
|  | 4 | Transparent liquid | Transparent liquid | Transparent liquid |
|  | 5 | Transparent liquid | Transparent liquid | Transparent liquid |
|  | 6 | Transparent liquid | Transparent liquid | Transparent liquid |
|  | 7 | Transparent liquid | Transparent liquid | Transparent liquid |
|  | 8 | Transparent liquid | Transparent liquid | Transparent liquid |
|  | 9 | Transparent liquid | Transparent liquid | Transparent liquid |
|  | 10 | Transparent liquid | Transparent liquid | Transparent liquid |
|  | 11 | Transparent liquid | Transparent liquid | Transparent liquid |
|  | 12 | Transparent liquid | Transparent liquid | Transparent liquid |
|  | 13 | Transparent liquid | Transparent liquid | Transparent liquid |

TABLE 9

Evaluation of Stability under Refrigeration of Comparative Examples 1 to 3

|  |  | During preparation | 1 Week | 2 Weeks |
|---|---|---|---|---|
| Comparative Examples | 1 | Transparent liquid | Transparent liquid | Precipitate formed |
|  | 2 | Transparent liquid | Transparent liquid | Precipitate formed |
|  | 3 | Transparent liquid | Transparent liquid | Precipitate formed |

As shown in tables 6 to 9, the ophthalmic compositions of Examples 1 to 13 comprising the cyclodextrin derivative (hydroxypropylbetadex) that is an anti-recrystallizing agent were colorless and transparent even after standing for a long time, while precipitates were formed that does not comprise the anti-recrystallizing agent in the compositions of Comparative Examples 1 to 5 after 2 weeks.

Experimental Example 2

In order to determine the availability of amino acids as an anti-recrystallizing agent, the compositions prepared in Examples 14 to 21 were stored at room temperature and under refrigeration, and then the presence or absence of crystal precipitation over time was determined by the same method as Experimental Example 1 and shown in the following tables 10 and 11.

TABLE 10

Evaluation of Stability at Room Temperature of Examples 14 to 21

| Room Temperature |  | During preparation | 1 Day | 2 Weeks | 4 Weeks |
|---|---|---|---|---|---|
| Examples | 14 | Transparent liquid | Transparent liquid | Transparent liquid | Transparent liquid |
|  | 15 | Transparent liquid | Transparent liquid | Transparent liquid | Transparent liquid |
|  | 16 | Transparent liquid | Transparent liquid | Transparent liquid | Transparent liquid |
|  | 17 | Transparent liquid | Transparent liquid | Transparent liquid | Transparent liquid |
|  | 18 | Transparent liquid | Transparent liquid | Transparent liquid | Transparent liquid |
|  | 19 | Transparent liquid | Transparent liquid | Transparent liquid | Transparent liquid |
|  | 20 | Transparent liquid | Transparent liquid | Transparent liquid | Transparent liquid |
|  | 21 | Transparent liquid | Transparent liquid | Transparent liquid | Transparent liquid |

TABLE 11

Evaluation of Stability under Refrigeration of Examples 14 to 21

| Room Temperature | | During preparation | 1 Week | 2 Weeks | 4 Weeks |
|---|---|---|---|---|---|
| Examples | 14 | Transparent liquid | Transparent liquid | Transparent liquid | Transparent liquid |
| | 15 | Transparent liquid | Transparent liquid | Transparent liquid | Transparent liquid |
| | 16 | Transparent liquid | Transparent liquid | Transparent liquid | Transparent liquid |
| | 17 | Transparent liquid | Transparent liquid | Transparent liquid | Transparent liquid |
| | 18 | Transparent liquid | Transparent liquid | Transparent liquid | Transparent liquid |
| | 19 | Transparent liquid | Transparent liquid | Transparent liquid | Transparent liquid |
| | 20 | Transparent liquid | Transparent liquid | Transparent liquid | Transparent liquid |
| | 21 | Transparent liquid | Transparent liquid | Transparent liquid | Transparent liquid |

As a result of the experiment, the ophthalmic compositions of Examples 14 to 21 further comprising the amino acid also maintained the transparency (colorlessness) without any precipitate being formed.

Experimental Example 3

In order to determine the effect of the addition of thickener, the compositions prepared in Examples 22 to 29 were stored at room temperature and under refrigeration, and then the presence or absence of crystal precipitation over time was determined by the same method as Experimental Example 1 and shown in the following tables 12 and 13.

TABLE 12

Evaluation of Stability at Room Temperature of Examples 22 to 29

| | | During preparation | 1 Week | 2 Weeks | 4 Weeks |
|---|---|---|---|---|---|
| Examples | 22 | Transparent liquid | Transparent liquid | Transparent liquid | Transparent liquid |
| | 23 | Transparent liquid | Transparent liquid | Transparent liquid | Transparent liquid |
| | 24 | Transparent liquid | Transparent liquid | Transparent liquid | Transparent liquid |
| | 25 | Transparent liquid | Transparent liquid | Transparent liquid | Transparent liquid |
| | 26 | Transparent liquid | Transparent liquid | Transparent liquid | Transparent liquid |
| | 27 | Transparent liquid | Transparent liquid | Transparent liquid | Transparent liquid |
| | 28 | Transparent liquid | Transparent liquid | Transparent liquid | Transparent liquid |
| | 29 | Transparent liquid | Transparent liquid | Transparent liquid | Transparent liquid |

TABLE 13

Evaluation of Stability under Refrigeration of Examples 22 to 29

| | | During preparation | 1 Week | 2 Weeks | 4 Weeks |
|---|---|---|---|---|---|
| Examples | 22 | Transparent liquid | Transparent liquid | Transparent liquid | Transparent liquid |
| | 23 | Transparent liquid | Transparent liquid | Transparent liquid | Transparent liquid |
| | 24 | Transparent liquid | Transparent liquid | Transparent liquid | Transparent liquid |
| | 25 | Transparent liquid | Transparent liquid | Transparent liquid | Transparent liquid |
| | 26 | Transparent liquid | Transparent liquid | Transparent liquid | Transparent liquid |
| | 27 | Transparent liquid | Transparent liquid | Transparent liquid | Transparent liquid |
| | 28 | Transparent liquid | Transparent liquid | Transparent liquid | Transparent liquid |
| | 29 | Transparent liquid | Transparent liquid | Transparent liquid | Transparent liquid |

As a result of the experiment, it was observed that the compositions further comprising the thickener also maintained the transparency (colorlessness) and stability during the observation period.

Experimental Example 4

In order to determine the effect of the addition of solubilizing agent, the compositions prepared in Examples 30 to 34 were stored at room temperature and under refrigeration, and then the presence or absence of crystal precipitation over time was determined by the same method as Experimental Example 1 and shown in the following tables 14 and 15.

TABLE 14

Evaluation of Stability at Room Temperature of Examples 30 to 34

| | | During preparation | 1 Week | 2 Weeks |
|---|---|---|---|---|
| Examples | 30 | Transparent liquid | Transparent liquid | Transparent liquid |
| | 31 | Transparent liquid | Transparent liquid | Transparent liquid |
| | 32 | Transparent liquid | Transparent liquid | Transparent liquid |
| | 33 | Transparent liquid | Transparent liquid | Transparent liquid |
| | 34 | Transparent liquid | Transparent liquid | Transparent liquid |

TABLE 15

Evaluation of Stability under Refrigeration of Examples 30 to 34

| | | During preparation | 1 Week | 2 Weeks |
|---|---|---|---|---|
| Examples | 30 | Transparent liquid | Transparent liquid | Transparent liquid |
| | 31 | Transparent liquid | Transparent liquid | Transparent liquid |
| | 32 | Transparent liquid | Transparent liquid | Transparent liquid |
| | 33 | Transparent liquid | Transparent liquid | Transparent liquid |
| | 34 | Transparent liquid | Transparent liquid | Transparent liquid |

As a result of the experiment, it was observed that the compositions further comprising the solubilizing agent also maintained the transparency (colorlessness) and stability during the observation period.

The invention claimed is:
1. An ophthalmic composition comprising:
rebamipide;
consisting of a single amino acid, wherein the single amino acid consists of arginine;
a buffering agent, the ophthalmic composition being transparent solution and preventing the formation of a precipitate layer; and
wherein the pH range of the ophthalmic composition is between 7 and 8, the ophthalmic composition being transparent and free of precipitation of said rebamipide for at least 16 weeks.

2. The ophthalmic composition of claim 1, wherein the concentration of rebamipide is 0.1 to 1.5 w/v %.

3. The ophthalmic composition of claim 1, wherein the concentration of the arginine is 0.1 to 5.0 w/v %.

4. The ophthalmic composition of claim 1, wherein the buffering agent is selected from the group consisting of borate, phosphate, tromethamine, and mixtures thereof.

5. The ophthalmic composition of claim 1, wherein the concentration of the buffering agent is 0.05 to 2.0 w/v %.

6. The ophthalmic composition of claim 1, further comprising at least one additive selected from the group consisting of a thickener, a solubilizing agent, an isotonic agent, and a pH adjusting agent.

7. The ophthalmic composition of claim 1, wherein the composition is a solution.

\* \* \* \* \*